United States Patent [19]
Rohrbough

[11] Patent Number: 5,324,258
[45] Date of Patent: Jun. 28, 1994

[54] RESERVOIR MODULE FOR A DRUG DELIVERY SYSTEM

[75] Inventor: John Rohrbough, Scottsdale, Ariz.

[73] Assignee: F. H. Faulding & Co. Limited, Parkside, Australia

[21] Appl. No.: 7,619

[22] Filed: Jan. 22, 1993

[30] Foreign Application Priority Data

Jan. 30, 1992 [AU] Australia ............................ PL0611

[51] Int. Cl.$^5$ ........................................... A61M 37/00
[52] U.S. Cl. .................................... 604/86; 604/151; 604/411; 604/415
[58] Field of Search ................ 604/86, 122, 123, 129, 604/131-133, 140, 141, 143, 146, 147, 148, 149, 150, 151, 152, 154, 207, 208, 232-234, 236, 244, 249, 403, 404, 411, 415, 201, 203, 205, 206, 213, 214, 218; 222/251, 257, 282, 566

[56] References Cited

U.S. PATENT DOCUMENTS

| | | | |
|---|---|---|---|
| 3,321,098 | 5/1967 | Ogle | 604/415 |
| 3,994,296 | 11/1976 | Cloyd . | |
| 4,169,475 | 10/1979 | Genese . | |
| 4,199,307 | 4/1980 | Jassawalla | 604/153 |
| 4,259,956 | 4/1981 | Ogle | 604/415 |
| 4,559,038 | 12/1985 | Berg et al. . | |
| 4,565,542 | 1/1986 | Berg . | |
| 4,650,469 | 3/1987 | Berg et al. . | |
| 4,657,486 | 4/1987 | Stempfle . | |
| 4,883,483 | 11/1989 | Lindmayer . | |

FOREIGN PATENT DOCUMENTS

9003505 5/1990 Fed. Rep. of Germany .
2200022 9/1973 France .
WO84/00893 8/1983 PCT Int'l Appl. .

OTHER PUBLICATIONS

CADD—PCA—Ambulatory Fusion Pump Model 5800 (page from advertisement).
U.S. Patent Office Official Gazette, Mar. 15, 1988, p. 1524, Pat. No. 294,733, Casing for a Drug Delivery System.
Abbott Lifecare 4100 (page from brochure).

Primary Examiner—John D. Yasko
Assistant Examiner—N. Kent Gring
Attorney, Agent, or Firm—Darby & Darby

[57] ABSTRACT

A medicament reservoir module for attachment to a pumping and control module includes a conventional medicament vial closed at one end by a penetrable stopper, which is inserted to operate as a piston in the vial. A hollow needle, attached to an adaptor that releasibly connects to the stopper, pierces the stopper and provides a medicament flow path via a slack length of flexible tubing from the vial to a peristaltic pump in the pumping and control module. A housing supports the vial, encloses the adaptor, hollow needle, and slack tubing, and releasibly connects to the pumping and control module. Thereby, a detachable reservoir module is provided, permitting quick and reliable resupply of medicament directly from filled standard vials.

20 Claims, 3 Drawing Sheets

RESERVOIR MODULE FOR A DRUG DELIVERY SYSTEM

BACKGROUND OF THE INVENTION

The present invention relates to a drug delivery system, particularly a system utilizing pumps of the negative pressure type for continuous delivery of drugs.

It is known in the prior art to administer fluids to a patient in a number of ways. For example, a solution such as saline, glucose or an electrolyte in a glass or flexible container is fed intravenously by gravity to a patient's venous access site via a length of flexible plastic tubing such as polyvinylchloride tubing. Flow from the container to the patient may be regulated by means of a roller clamp.

However, such gravity-feed type systems are of limited application. This is particularly so where continuous or controlled application of drugs is required. For example, in the treatment of pain related conditions, it is known in the art to use a number of electro-mechanical pumping systems to deliver drugs to the patient. A number of positive pressure pumps, e.g. of the plunger type, are known in the field. An example thereof is the pump sold under the trade designation "Lifecare PCT+2 Infusion System" available from Abbott Laboratories. However, such positive feed systems suffer from a number of difficulties. For example, with positive pressure systems, after the pump stops, flow contents of the system may continue to be expelled or sucked back because of the positive pressure already created in the syringe, thus making control less accurate. Further, with systems such as the Abbott Lifecare system, specially designed drug vials must be utilized.

It is also known in the prior art to utilize negative pressure pump systems for the delivery of drugs. The drug is drawn from a vial rather than being expelled. For example, a peristaltic pumping action is particularly well suited for this purpose. An advantage is provided because peristaltic pumping action may be applied externally of the tubing carrying the intravenous or like fluid. Thus, sterile conditions of the fluid are maintained within the tubing while imparting propulsion to the fluid. Also, the peristaltic pumping action may be applied at any point along the tubing.

In a common type of peristaltic pump known in the prior art, a driving motor is connected to an array of cams angularly spaced from each other. The cams in turn drive cam followers connected to corresponding pressure fingers, which act on a flexible tubing that is carrying the intravenous fluid. The pump elements cooperate to impart a linear wave motion on the pressure fingers that moves the fluid along in a pulsatile flow.

Whereas such negative pressure systems provide significant advantages over the positive pressure systems known in the art, difficulties still remain with the peristaltic pump type arrangements. For example, containers utilized with the peristaltic systems are flexible bags, which are initially empty and which must be filled with fluid by the operator. Such containers are inconvenient to fill, difficult to use, and increase the danger of inadvertent spillage or contamination.

SUMMARY OF THE INVENTION

According to the present invention there is provided an adaptor including an inlet end and an outlet end and defining a drug fluid pathway extending longitudinally therethrough. A connection nozzle is provided at the outlet end. A connection socket or recess in the inlet end of the adaptor connects to a penetrable stopper of a cylindrical medicament vial, which has a closed end and an open end that is closed by the penetrable stopper.

A tubular spike, that is, a hollow needle, protrudes from the adaptor socket and extends beyond the inlet end of the adaptor. The needle is arranged, in use, to penetrate the stopper and to provide a fluid flow connection between the vial and the fluid pathway.

The adaptor outlet nozzle connects to a flexible tubing through which fluid from the vial is delivered to the patient.

A pumping device of the peristaltic type, operates on a length of the tubing that connects to the nozzle of the adaptor and is arranged, in use, to provide a flow connection, from the adaptor to the patient in a fluid tight arrangement. The suction delivery, i.e. pumping, device applies a smooth peristaltic pumping action to the exterior of the tubing to provide propulsion of the liquid at the interior of the tubing without risk of fluid contamination.

A plurality of adaptor-vial units may be connected in parallel to increase the capacity of the suction delivery device to deliver fluids over an extended time period. The rate of flow is determined by the pump and not by the number of adaptor-vial units that are connected to the pump at the same time.

For operation of the drug delivery system, a medicament-containing vial, sealed by its stopper, is screwed onto the adaptor. In the screwing process, the hollow needle penetrates the stopper to provide access to the flow pathway for the liquid in the vial. When the vial is empty, it is unscrewed from the adaptor and can be replaced with another filled vial. The medicament vial may be of a standard known type.

Withdrawal of fluid from the vial, through the hollow needle, by action of the pumping device, reduces the pressure within the vial. The reduced internal pressure causes the joined stopper and adaptor to slide into the vial, in piston-like manner, under the influence of the external ambient pressure as the fluid in the vial is withdrawn. Thus, a vacuum, which would prevent operation of the pump, is not created in the vial as the liquid is drawn out.

In accordance with the invention, a housing is provided which encloses the vial and adaptor, and forms a reservoir module adapted to interface with the pumping device. This reservoir module connects to the housing of the pumping device so that a single integrated drug delivery system is provided by the combination.

Accordingly, it is an object of the present invention, to eliminate the need to use the special flexible bags or container for supplying medicament to the drug delivery systems of the prior art.

Another object of the present invention is to provide an improved drug delivery system that uses conventional, available medicament vials in a negative pressure pumping system.

Still another object of the invention is to provide an improved drug delivery system wherein vials are easily replaced.

Yet another object of the invention is to provide a standardized reservoir module, comprising a filled medicament vial, that is adapted to be easily connected to a conventional pumping unit.

The invention accordingly comprises the features of construction, combination of elements and arrangements of parts which will be exemplified in the constructions hereinafter set forth and the scope of the invention will be as indicated in the claims.

BRIEF DESCRIPTION OF THE DRAWINGS

For a fuller understanding of the invention, reference is had to the following description taken in connection with the accompanying drawings in which.

DESCRIPTION OF THE PREFERRED EMBODIMENTS

Figure 1:
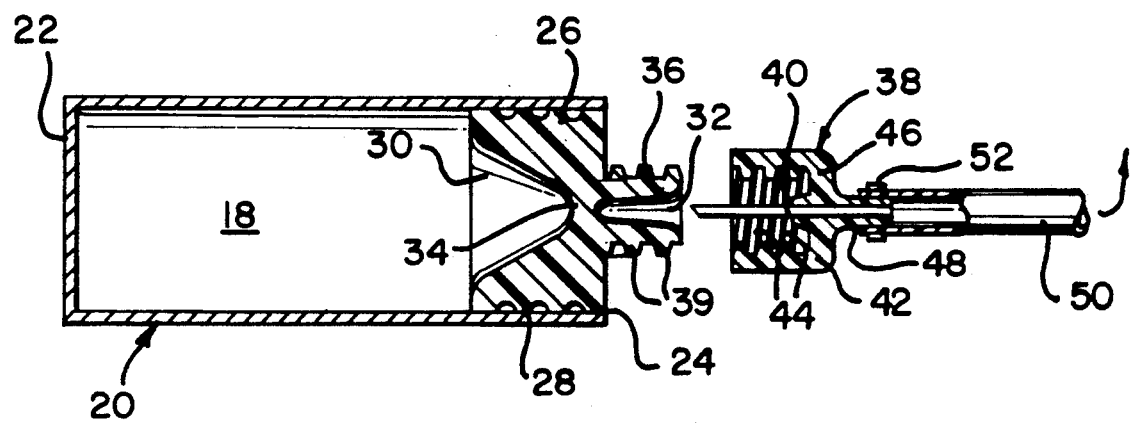
FIG. 1 is a side elevational view in cross section of an adaptor and vial in accordance with the invention.

With reference to the Figures, a drug delivery system 10 in accordance with the invention includes a pumping unit 12 of the suction type and a drug reservoir module 14 of the suction type, mechanically joined together to form an integrated package. A delivery tube 16, in use of the system, carries a metered flow of liquid medicament to a patient.

Fluid 18, e.g. medicine, stored in a cylindrical vial 20 having a closed end or base 22 and an open end 24, which is sealed with a penetrable stopper 26 that fits within the vial to serve as a sliding piston. Annular peripheral ridges 28 on the stopper 26 assure a good seal between the inner walls of the vial 20 and stopper 26 so that the stored fluid 18 cannot escape or be contaminated during storage, handling, shipment and use of the vial. The vial 20 may be of conventional design and construction as available, for instance, from David Bull Laboratories Pty. LTD (Mulgrave, Australia). The stopper 26 is of resilient material so that it is readily punctured by a spike or hollow needle, thereby giving access to the fluid 18. For this purpose, the stopper 26 includes opposed recesses 30,32 which are separated by a relatively thin septum 34 for penetration by a needle. A neck 36 on the stopper has external threads 38, which are smaller in diameter than the inside diameter of the vial.

An adaptor 38 includes a hollow spike or needle 40 that is mounted on a cup-shaped collar 42. The collar 42 has an internal cylindrical wall with threads 44 suitable for engagement with the threads 38 on the neck 36 of the stopper 26. The needle 40 extends through the rear wall 46 of the adaptor 38 and through an integral cylindrical stem or nozzle 48 to which a resilient tubing 50 connects. A seal 52 at the connection between the tubing 50 and the stem 48 assures that none of the fluid leaving the needle 40 escapes. Conventional, releasable, sealing means are utilized as are available in presently available drug delivery systems. The seal 52 may include a clamp around the outside of the tube and may include an O-ring. Construction of the seal is not a novel portion of the invention and, accordingly, is not described in detail herein.

The outside diameter of the adaptor 38 is less than the inside diameter of the vial 20 so that the adaptor, in use, may enter the vial 20 with the stopper 26 when the fluid 18 is withdrawn through the adaptor 38, as described more fully hereinafter.

The length of the neck 36 on the stopper 26 and the length and protrusion of the needle or tubular spike 40 are such that when the neck 36 of the stopper 26 is threaded into the collar 42, the needle 40 penetrates the stopper 26 at its thinnest portion 34, whereby, access is provided to the fluid 18. When the pressure in the tubing 50 is reduced by pumping action, fluid 18, that may be a medicine, is withdrawn from the vial 20 by way of the hollow needle 40. This withdrawal of fluid 18 reduces the pressure within the vial 20. Then ambient pressure acting on the outside of the vial 20 and on the exposed surfaces of the stopper 26, causes the stopper 26 to move, as a piston, further into the vial 20 in the direction of the closed end 22. Thus, fluid 18 can be withdrawn at a controlled rate from vial 20 until the supply is exhausted, so long as ambient pressure is exerted on the external surfaces of the stopper 26. Because both the stopper 26 and the collar 42, may enter the vial 20, in use, it is necessary that the outer diameters of these elements not exceed the internal diameter of the vial.

Figure 2:
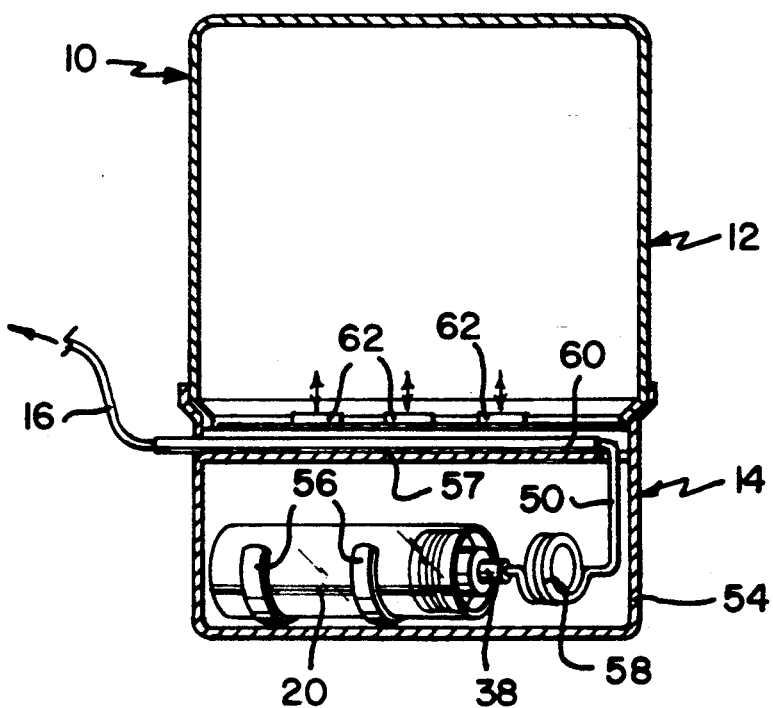
FIG. 2 is a drug delivery system including a reservoir module in accordance with one embodiment of the invention, incorporating the adaptor and vial combination of FIG. 1.

In the embodiment illustrated in FIG. 2, a housing 54 encloses the connected vial 20 and adaptor 38 to define the reservoir module 14. The vial 20 is held in place in the housing by clamps 56 that are fixedly connected to the housing 54. The housing 54 may be similar to the housing in U.S. Pat. No. 4,565,542 and connected to the control module of the patent in the same manner. The tubing 50 leads to an external top surface 57, which is in close proximity with pumping unit 12 when the reservoir module 14 is clamped unto the control module. An intermediate coil 58 of tubing is located in the fluid flow path between the vial 20 and the pumping unit 12. When the adaptor 38 enters the vial 20 under the influence of external pressure and the fluid within the vial 20 is withdrawn through the tubing 50,58, by action of the pumping unit on the tubing portion 60, the tubing coil 58 tends to stretch like a coil spring. Expansion of the tubing coil 58 during use assists in preventing collapse of the tubing under reduced internal pressure and also provides slack to permit easy replacement of empty vials.

From the coil 58, a non-collapsible section 60 of tubing leaves the interior of the reservoir module housing 54 and extends along the outer top surface 57 so as to be adjacent the exposed lower portion of the pumping unit 12. This tubing 60 is operated upon by a peristaltic pump of the linear type, indicated schematically in FIG. 2 as including reciprocating cams 62, which, by their proper sequencing in a known manner, provide a pumping action that moves the fluid through tube 50,60 from the vial 20 to the delivery tube 16. In an alternative embodiment (not shown) in accordance with the invention, a rotating peristaltic pump may be used.

The housing 54 is adapted for snap-fit connection to the housing of the pumping unit 12, although any other mechanical connection may be used. Although not preferred, there need not be any mechanical connection between the reservoir module 14 and the pumping unit 12 other than that the fluid-carrying tubing 60 must be in such proximity to the peristaltic pump that the pump can operate on the tubing.

Figure 3:
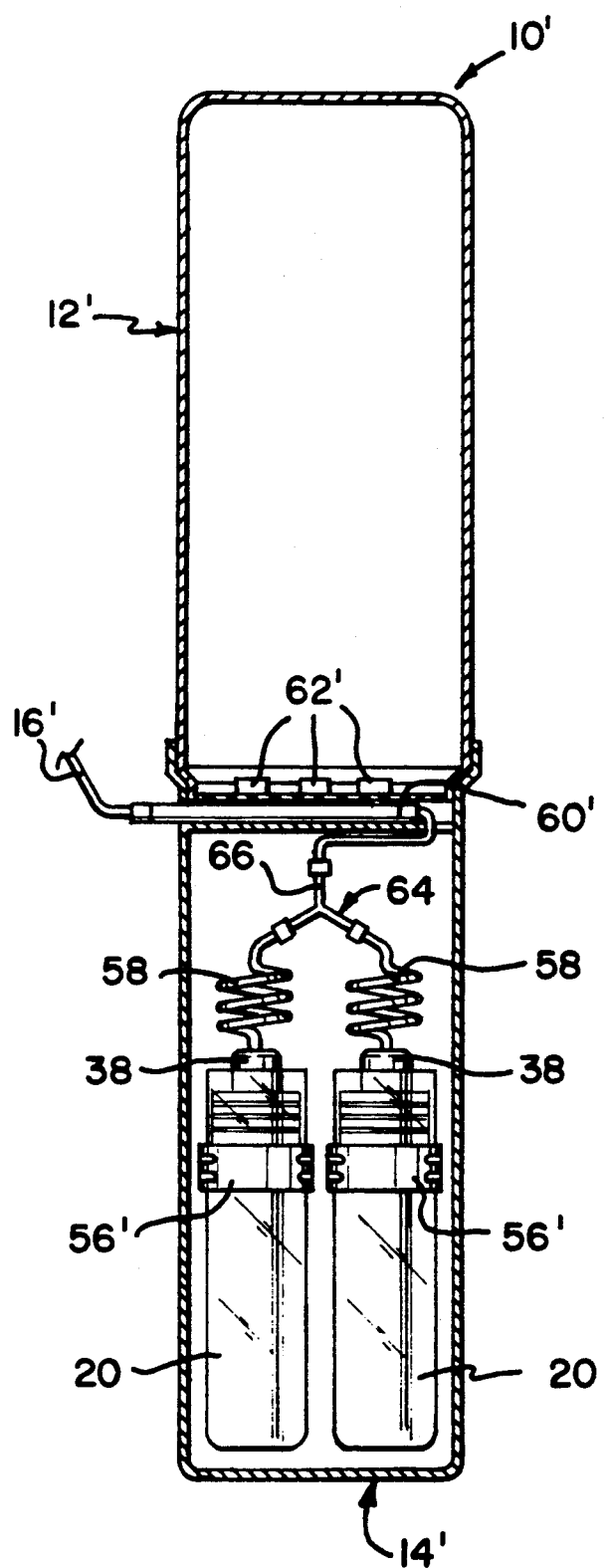
FIG. 3 is a drug delivery system having an alternative embodiment of a reservoir module in accordance with the invention, incorporating a plurality of adaptor and vial combinations in parallel.

In an alternative embodiment (FIG. 3) in accordance with the invention, a pumping unit 12' is connected to a reservoir module 14' having a pair of vials 20 with adaptors 38 arranged in parallel. Flow from each vial 20 passes through a respective tubing coil 58 and enters a branch of a Y-fitting 64. The third branch 66 of the Y-fitting 64 connects to a tubular section 60, that extends into the pumping unit 12' where it is acted upon by the cams 62' of a peristaltic pump, whereby fluid from the vials 20 is delivered to a delivery tube 16'. Thus, in this embodiment, with delivery at a set flow rate of fluid, time without need to change the vials 20, is approximately doubled.

It will be readily understood that the Y-fitting 64 may be replaced with a T-fitting and in another alternative embodiment, a manifold may be used to receive inputs from a plurality of vials 20 and deliver a single flow of liquid to the pumping unit 12'.

A critical needs exists to prevent leakage of fluid 18 to the external environment at any point in the delivery system between the vials and the patient. Also, there is a need to prevent ingress of air or other contaminants to the fluid pathway. To this end, special sealing devices may be incorporated, such as O-rings, where the tubular spike or needle 40 passes through the collar 42 of the adaptor 38. A seal is also required where the tube 50 joins to the stem or nozzle 48 on the adaptor. A seal is also needed where the external delivery tube 16 connects to an extension of the tubing section 60 from the peristaltic pump, and where the tubing from the coil 58 connects to the tubing section 60 in the pumping unit 12. The necessity for seals and designs for such seals are well known to those skilled in the art and accordingly are not described herein in detail.

In using the drug delivery system 10, it is necessary to prime the tubing with liquid after the adaptor 38 is connected to the cylindrical medicament vial 20 and the tubular spike or needle 40 has penetrated the penetrable stopper 26. Priming may be achieved by standing the vial on its base 22, adaptor 38 on top, and depressing the adaptor. This causes fluid to flow into the tubing 50 by way of the hollow needle 40 and the device is primed for operation when liquid reaches the peristaltic pump. The coil 58 is advantageous in this procedure.

After the pumping unit 12 is turned ON so that the peristaltic pump operates, fluid is drawn from the vial 20. The negative pressure in the vial 20, created by removal of the fluid, causes the stopper 26 to progress toward the vial base 22. The stopper 26 is able to move along the inside cylindrical surface of the vial 20 because the priming operation, that is, pressing on the adaptor 38, breaks an initial friction set between the stopper ridges 28 and the inside surface of the vial 20.

The suction pumping operation provided by the pumping unit 12 causes liquid transfer from the cylindrical medicament vial 20 via the adaptor 38 to the patient, and simultaneously compensating stopper longitudinal movement relative to the vial 20 under external atmospheric pressure, reduces the chamber volume of the vial 20 by an amount generally equal to the liquid transfer.

In order to assist in moving the adaptor into the vial in the priming step, the adaptor 38 may include at least one finger tab (not shown) on its outer surface. Preferably, the adaptor includes a pair of finger tabs mounted on opposite sides of the adaptor 38. The person priming the pump presses on the finger tab, or tabs, which may be formed integrally with the adaptor. However, the finger tabs must not interfere with motion of the adaptor 38 into the vial 20. Additionally, because proper operation of the vial/adaptor combination depends on forces produced by the ambient atmosphere, it is necessary that the reservoir module 14 provide entry for atmospheric air into the housing. For this purpose, a hydrophobic filter may be used over an opening in the housing.

It has been found that by attaching a pair of cylindrical vials 20 in parallel utilizing a junction member 64, the linear peristaltic action of a suction type pump creates a negative pressure in the tubing which sucks fluid from either of the vials. Accordingly, if one vial empties before the other, the pump automatically draws fluid from the other vial.

The housing 54 and the pumping unit 12 apparatus may be adapted for snap-fit connection and the housing may be formed of a plastics material, and may also function to provide containment of fluid should the cylindrical medicament vial or vials suffer a breakage.

Figure 4:
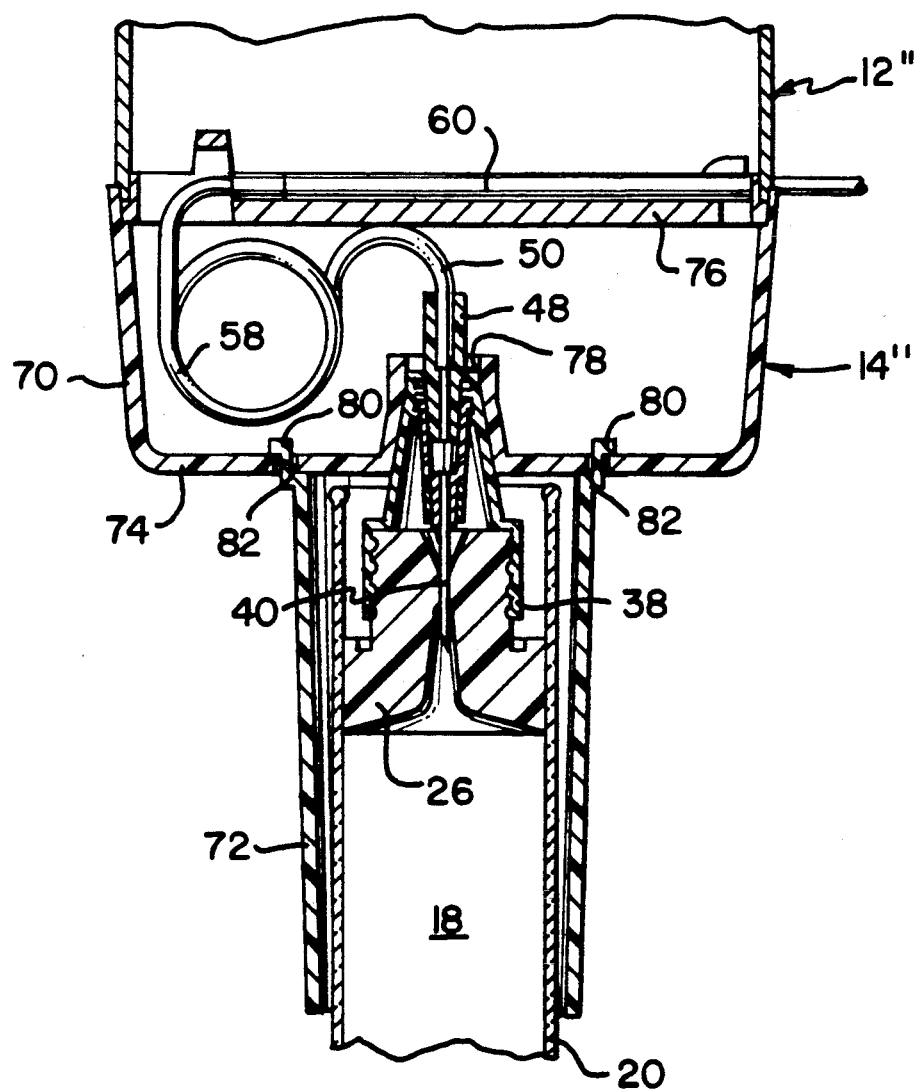
FIG. 4 is a partial view in section of a drug delivery system having a further embodiment of a reservoir module in accordance with the invention for permitting quick replacement of medicament vials.

In another alternative embodiment (FIG. 4) in accordance with the invention, a pumping unit 12" connects to a reservoir module 14" that includes a tube housing 70 and a vial housing 72.

A medicament vial 20 is located within the vial housing 72 with the stopper 26 facing upward toward a base 74 of the tube housing 70. Also within the vial housing 72 is an adaptor 38 including the hollow needle 40. However, the adaptor 38 has no fixed connection to the vial housing, but is instead connected by the tubing 50,58 to the tubing 60, which is proximate the peristaltic pump in the pumping unit 12, as described above.

The tubing portion 60 that is subject to direct pumping action by the peristaltic pump, rests on the top surface 76 of the tube housing 70, and the coiled portion 58 of tubing is enclosed in the housing 70. A recessed opening 78 in the base 74 allows the tubing 50 to extend into the vial housing 72 as medicament 18 is withdrawn from the vial 20, and the stopper 26 and adaptor 30 progressively move into the vial under influence of ambient pressure on the stopper 26.

The reservoir module 14" connects to the pumping unit 12 by any suitable means that provides the required interface between the medicament filled tubing 60 and the internal peristaltic pump (not shown) of the pumping unit 12, as described above with reference to FIG. 2. A snap-fit connection, for example, may releasibly secure the housing 70, and thereby, the entire reservoir module 14", to the pumping unit 12.

Tabs 80 positioned around the top periphery of the housing 72 releasibly engage in registered openings 82 in the base 74 of the tube housing 70. Thus, the housings 70,72 are quickly and easily separated, whereby an empty vial 20 may easily be removed and replaced by another filled vial without need to disengage the tube housing 70 from the pumping unit 12.

Thus, the pump-to-tubing interface between the pumping unit 12 and reservoir module 14" is not disturbed when exchanging vials. The slack in the tubing provided in part by the coiled portion 58 facilitates vial removal and the simple connection of the adaptor 38 to a new vial.

The length of the housing 72 corresponds to the vial length so that the position of the vial 20 is substantially fixed in the assembled reservoir module 14". Vials of different lengths may be used with the module 14" by having several interchangeable housings 72 of differing lengths, and sufficient tube lengths 50,58. On the other hand, in an alternative embodiment, the vial housing 72 may contain spring means (not shown) that act on the vial base 22, whereby vials of different lengths may be accommodated in the housing 72 with stability.

The cylindrical medicament vial 20 may be of a standard known type, made of glass, to hold a pharmaceutical product such as a narcotic drug. The narcotic drug may be selected from one or more of morphine, meperidine, fentanyl, hydromorphone and the like.

The pharmaceutical may also, by way of example, include an anti. cancer formulation. The anti-cancer formulation may be selected from one or more of doxorubicin, cytarabine, vinblastine, cisplatin, bleomycin, mitomycin or the like.

The adaptor 38 is fabricated from conventional materials and components. A plastics material may be used for general construction thereof, for example, formed by injection molding. The hollow tubular spike or needle 40 is preferably of metal, e.g. stainless steel.

The adaptor is generally circular in cross section and the stem or nozzle 48 is generally cylindrical. However, the nozzle 48 may taper toward its discharge end.

The tubing 50,58,60 may be of any suitable type that is flexible and non-collapsible when internal pressure is reduced during operation of the pump. The tubing may have a small bore so that the priming volume is reduced. A non-kinking microbore type of tubing is preferred.

In a preferred embodiment, the tubing may include a calibrated section (not shown) in the region of the pump to permit accurate fluid delivery to the patient. Such a section may be formed of a silicone type material, at least in the region of the pump, and a silastic type material is preferred.

Use of peristaltic pumps of the linear and rotary types has been mentioned. Other pumps may be used in alternative embodiments. However, peristaltic pumps have been known for the accuracy and uniformity of their output. A peristaltic pump under the trade name Deltec Cadd-PCT, which is available from Pharmacia Corporation of Saint Paul, Minn., has been found to provide satisfactory performance.

The drug delivery system 10 is particularly suitable for Patient Controlled Analgesia (PCA) and like applications. The system 10 may be provided in a ready-to-use kit form, which may include one or more adaptors 38, one or more filled cylindrical medicament vials 20, and a pumping unit 12 incorporating tubing arrangements as described above. Such kits are particularly suitable for use both in hospital and home treatment environments. Standard vials 20 can be utilized in the kit. The reservoir module 14 may be a kit independent of the pumping unit 12.

The drug delivery system 10 in accordance with the invention is gravity independent and therefore will operate satisfactorily regardless of orientation. The position of the pumping unit 12 relative to the reservoir module 14 is not critical. As illustrated, the pumping unit 12 is above the reservoir module 14. However, the positions may be reversed. Also, the reservoir module 14 may be alongside, in front of, behind, etc., the pumping unit 12 in alternative embodiments in accordance with the invention.

It will thus be seen that the objects set forth above, among those made apparent from the preceding description, are efficiently obtained and, since certain changes may be made in the above constructions without departing from the spirit or the scope of the invention, it is intended that all matter contained in the above description, or shown in the accompanying drawings shall be interpreted as illustrative and not in a limiting sense.

What is claimed is:

1. A medicament reservoir module for attachment to a pumping unit containing pumping means and control mechanism for a drug delivery system, said reservoir module, comprising:

a housing adapted for releasable connection to said pumping unit and for supporting a vial of liquid medicament intended for use in said drug delivery system, said vial having length and being closed at one end by a base and having an open second end and a penetratable vial stopper movable as a piston in said vial;

an adaptor, including:

a collar having first means for attachment to said vial stopper and having second means for attachment to a medicament delivery tube;

a hollow needle mounted to said collar for penetrating said stopper when a vial is connected to said adaptor by said first means for attachment;

a flexible medicament delivery tube means having a first end connected to said second attachment means for movement with said adaptor, and a second end portion releasably fixed in relation to said housing for operative pumping engagement with said pumping means when said pumping unit is connected to said housing, said tube means being resilient and having clack between said second end portion thereof and said adaptor, permitting said adaptor to move a distance at least equal to the length of said vial.

2. A medicament reservoir module for a drug delivery system as in claim 1, wherein said first means for attachment includes a recess formed in said adapter, said needle extending from a base of said recess, a surface portion of said recess releasibly connecting with a surface portion of said penetrable stopper.

3. A medicament reservoir module for a drug delivery system as in claim 2, wherein said stopper and said recess are cylindrical and said surface portions of said stopper and said recess, are threaded with mating threads.

4. A medicament reservoir module for a drug delivery system as in claim 1, wherein a portion of said delivery tube is resiliently coiled to provide at least a portion of said slack.

5. A medicament reservoir module for a drug delivery system as in claim 1, wherein said second means for attachment on said adaptor is a cylindrical nozzle communicating with said needle and said delivery tube.

6. A medicament reservoir module for a drug delivery system as in claim 1, wherein said second end portion of said tubing is releasably fixed outside said housing, whereby said second end portion can be acted on by said pumping means when said housings and said pumping unit are connected together.

7. A medicament reservoir module for a drug delivery system as in claim 1, wherein said second end portion of said tube means is located adjacent the pumping means so that it is acted on lengthwise by said pumping means, which includes a peristaltic pump producing linear pumping action when said housing is connected to the pumping unit.

8. A medicament reservoir module for a drug delivery system as in claim 1, further comprising one of said medicament vials with said penetrable stopper in said second housing, said one vial being attached to said adaptor with said needle penetrating said stopper, whereby a continuous medicament flow path is provided between said vial and said delivery tube.

9. A medicament reservoir module for a drug delivery system as in claim 8, further comprising a second medicament vial in said second housing connected to a second adaptor and being connected in parallel with said one medicament vial to supply medicament flow to be acted on by said pumping means, said tube means including a tube connected to said second adaptor for forming said parallel flow path.

10. A medicament reservoir module for a drug delivery system as in claim 6, wherein said second tubing portion is acted on lengthwise by said pumping means, which includes a peristaltic pump producing linear pumping action.

11. A medicament reservoir module for attachment to a pumping unit containing pumping means and control mechanism for a drug delivery system, said reservoir module, comprising:
- a first housing for supporting a vial of liquid medicament intended for use in said drug delivery system, said vial having length and being closed at one end of a base and having an open second end and a penetratable stopper mounted as a piston in said vial;
- an adaptor including: a collar having first means for attachment to said vial stopper, and having second means for attachment to a medicament delivery tube;
- a hollow needle mounted to said collar for penetrating said stopper when a vial is connected to said adaptor by said first means for attachment;
- a second housing adapted for releasable connection at a first interface with said pumping unit and at a second interface with said first housing;
- a flexible medicament delivery tube means in said second housing, said tube means having a first end connected to said second attachment means for movement with said adaptor, and a second portion releasably fixed in relation to said second housing for operative pumping engagement with said pumping means at said first interface when said pumping unit is connected to said second housing, said tube means being resilient and having slack between said second end portion thereof and said adaptor, permitting said adaptor to move a distance at least equal to the length of said vial.

12. A medicament reservoir module for a drug delivery system as in claim 11, wherein said first means for attachment includes a recess formed in said one adaptor end, said needle extending from a base of said recess, a surface portion of said recess releasibly connecting with a surface portion of said penetratable stopper.

13. A medicament reservoir module for a drug delivery system as in claim 12, wherein said stopper and said recess are cylindrical and said surface portions of said stopper and said recess are threaded with mating threads.

14. A medicament reservoir module for a drug delivery system as in claim 11, wherein a portion of said delivery tube means is resiliently coiled in said second housing to provide at least a portion of said slack.

15. A medicament reservoir module for a drug delivery system as in claim 11, wherein said second means for attachment on said adaptor is a cylindrical nozzle communicating with said needle and said delivery tube.

16. A medicament reservoir module for a drug delivery system as in claim 11, wherein said second portion of said tube means is releasably fixed outside said second housing at said first interface, whereby said second portion can be acted on by said pumping means when said pumping unit and second housing are connected together.

17. A medicament reservoir module for a drug delivery system as in claim 11, wherein said second portion of said tube means is located adjacent the pumping means so that it is acted on lengthwise by said pumping means, which includes a peristaltic pump producing linear pumping action when said second housing is connected to the pumping unit.

18. A medicament reservoir module for a drug delivery system as in claim 11, further comprising one of said medicament vials with said penetrable stopper in said first housing, said one vial being attached to said adaptor with said needle penetrating said stopper, whereby a continuous medicament flow path is provided between said vial and said delivery tube means.

19. A medicament reservoir module for a drug delivery system as in claim 18, further comprising a second medicament vial in said first housing connected to a second adaptor and being connected in parallel with said one medicament vial to supply medicament flow to be acted on by said pumping means, said tube means including a tube connected to said second adaptor for forming said parallel flow path.

20. A medicament reservoir module for a drug delivery system as in claim 16, wherein said second portion of said tube means is acted on lengthwise by said pumping means, which includes a peristaltic pump producing linear pumping action.

* * * * *